United States Patent [19]
Schreiner et al.

[11] Patent Number: 5,840,875
[45] Date of Patent: Nov. 24, 1998

[54] KIDNEY NA/PO₄ COTRANSPORTER ANTISENSE OLIGONUCLEOTIDE

[75] Inventors: George F. Schreiner, Los Altos; Timothy W. Meyer, Palo Alto, both of Calif.; Rainer Oberbauer, Vienna, Austria

[73] Assignee: C.V. Therapeutics, Palo Alto, Calif.

[21] Appl. No.: 467,007

[22] Filed: Jun. 6, 1995

[51] Int. Cl.⁶ .............................. C07H 21/04; C12Q 1/68; C12N 5/06; A61K 31/70
[52] U.S. Cl. .......................... 536/24.5; 536/24.31; 435/6; 435/375; 514/4
[58] Field of Search ................................ 435/91.1, 240.2, 435/375, 6; 514/44; 536/23.1, 24.5, 24.3, 24.31

[56] References Cited

PUBLICATIONS

H. Tenenhouse et al., The American Society for Clinical Investigation, Inc., 93, pp. 671–676 (1994).
U. Laemmli, Nature, 227, pp. 680–685 (1970).
C. Allain et al., Clinical Chemistry, 20:4, pp. 470–475 (1974).
H. Towbin et al., Proc. Natl. Acad. Sci. USA, 76:9, pp. 4350–4354 (1979).
R. Stoll et al., Biochem. J., 180, pp. 465–470 (1979).
J. Emtage et al., Proc. Natl. Acad. Sci. USA, 80, pp. 3671–3675 (1983).
M. Jaye et al., Nucleic Acids Research, 11:8, pp. 2325–2335 (1983).
R. Labow et al., Biochimica et Biophysica Acta, 749, pp. 32–41 (1983).
A. Ullrich et al., The EMBO Journal, 3:2, pp. 361–364, (1984).
C. Brown et al., Biochimica et Biophysica Acta, 769, pp. 471–478 (1984).
E. Rudd et al., Biochimica et Biophysica Acta, 918, pp. 106–114 (1987).
J. Han et al., Biochemistry, 26, pp. 1617–1625 (1987).
D. Fitzpatrick et al., Journal of Virology, 62:11, pp. 4239–4248 (1988).
N. Abouakil et al., Biochimica et Biophysica Acta, 961, pp. 299–308 (1988).
L. Yakubov et al., Proc. Natl. Acad. Sci. USA, 86, pp. 6454–6458 (1989).
E. Christensen et al., Seminars in Nephrology, 11:4, pp. 414–439 (1991).
S. Agrawal et al., Proc. Natl. Acad. Sci. USA, 88, pp. 7595–7599 (1991).
J. Leonetti et al., Proc. Natl. Acad. Sci. USA, 88, pp. 2702–2706 (1991).
M. Simons et al., Nature, 359, pp. 67–71 (1992).
M. Ratajczak et al., Proc. Natl. Acad. Sci. USA, 89, pp. 11823–11827 (1992).
W. Gao et al., Molecular Pharmacology, 43, pp. 45–50 (1993).
L. Neckers et al., Am. J. Physiol. 265 (Lung Cell. Mol. Physiol. 9), pp. L1–L12 (1993).
C. Stein et al., Science, 261, pp. 1004–1012 (1993).
R. Morishita et al., Proc. Natl. Acad. Sci. USA, 90, pp. 8474–8478 (1993).
S. Magagnin et al., Proc. Natl. Acad. Sci. USA, 90, pp. 5979–5983 (1993).
P. Cossum et al., The Journal of Pharmacology and Experimental Therapeutics, 267:3, pp. 1181–1190 (1993).
A. Werner et al., The Journal of Biological Chemistry, 269:9, pp. 6637–6639 (1994).
J. Cohen, Advances in Pharmacology, 25, pp. 319–339 (1994).
N. Dean et al., Proc. Natl. Acad. Sci. USA, 91, pp. 11762–11766 (1994).
P. Zamecnik et al., Proc. Natl. Acad. Sci. USA, 91, pp. 3156–3160 (1994).
M. Custer et al., American Physiological Society, pp. F767–F774 (1994).
R. Wagner, Nature, 372, pp. 333–335 (1994).
Collins et al. "Molecular cloning, functional expression, tissue distribution, and in situ hybridization of the renal sodium phosphate (Na/Pi) transporter in the control and hypophosphatemic mouse" FASEB Journal 8: 862–868, Aug. 1994.
Gura "Antisense has growing pains" Science 270: 575–577, Oct. 1995.
Stull et al. "Antigene, ribozyme, and aptame nucleic acid drugs: Progress and prospects" Pharm. Res. 12: 465–481, Apr. 1995.
Uhlmann et al. "Antisense oligonucleotides: A new therapeutic principle" Chem. Rev. 90: 544–584, Jun. 1990.

*Primary Examiner*—John L. LeGuyader
*Assistant Examiner*—Thomas G. Larson
*Attorney, Agent, or Firm*—McDonnell Boehnen Hulbert & Berghoff

[57] ABSTRACT

This invention is a method for treating diseases involving the mammalian kidney proximal tubule epithelium with naked antisense oligonucleotides and antisense compositions against the mRNA of mammalian kidney epithelial proteins.

1 Claim, 10 Drawing Sheets

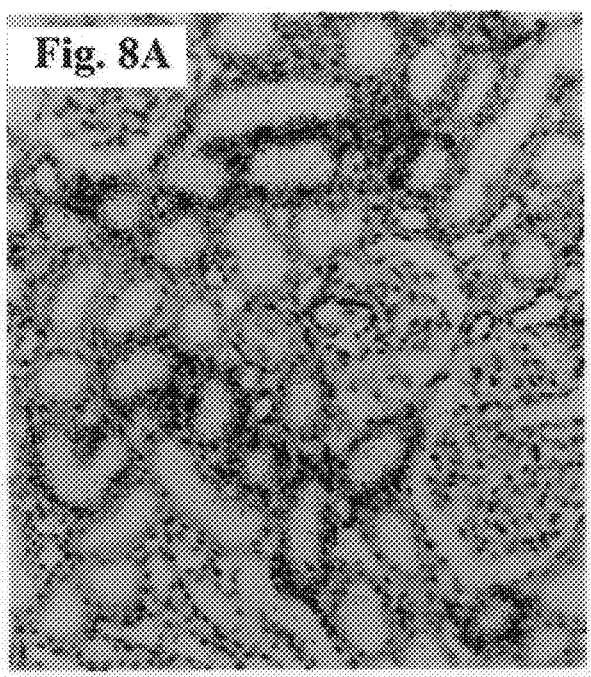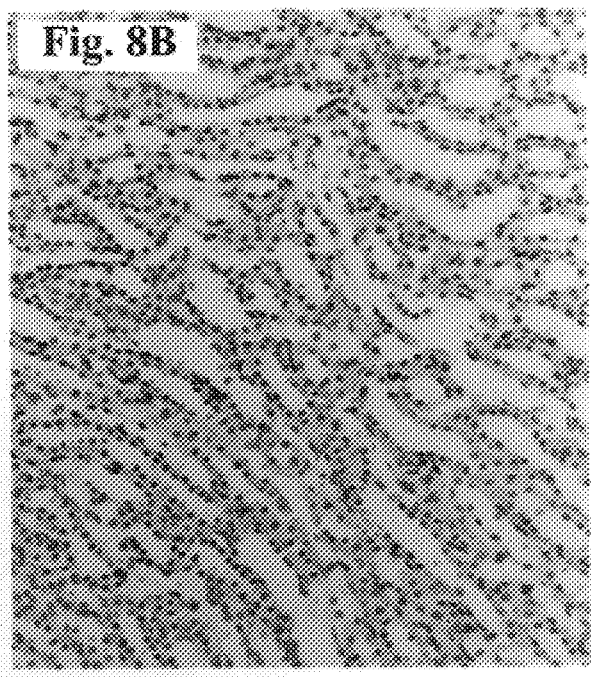

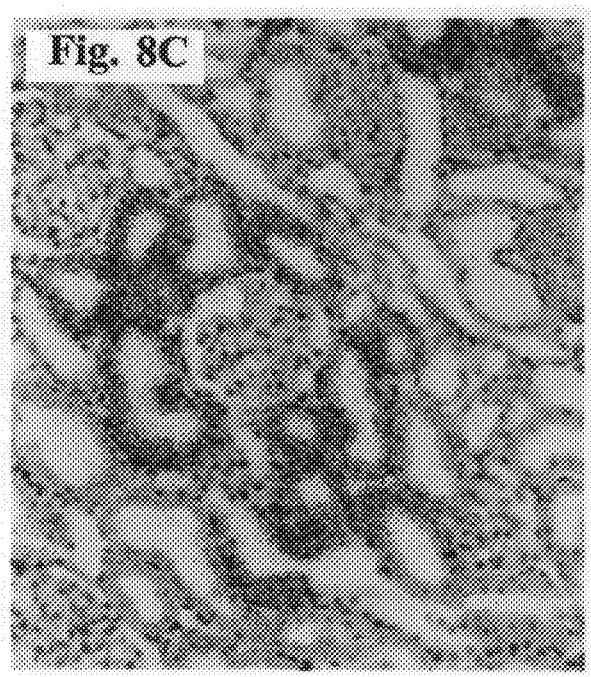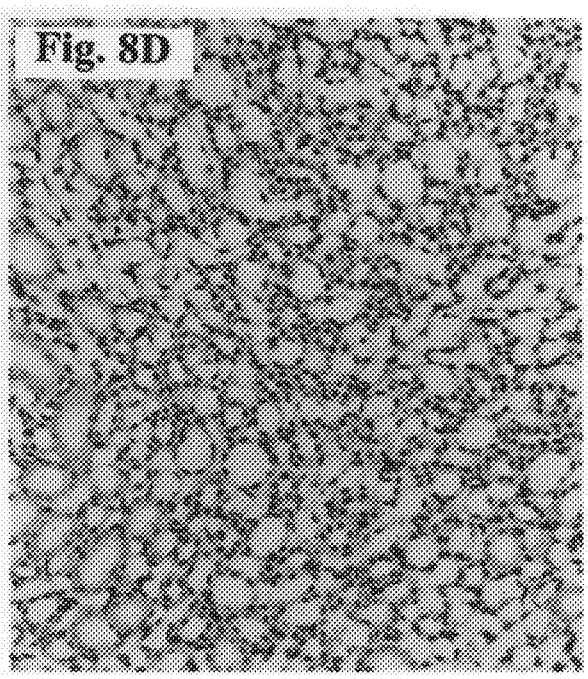

KIDNEY NA/PO₄ COTRANSPORTER ANTISENSE OLIGONUCLEOTIDE

BACKGROUND OF THE INVENTION

(1.) Field of the Invention

This invention is a method for using specific antisense oligonucleotides to treat diseases associated with the mammalian kidney. This invention is also a specific oligonucleotide that remains present and non-degraded in mammalian kidneys for extended periods of time.

(2.) Description of the Art

Antisense oligonucleotides offer a potential means to block expression of individual genes. The antisense effect of unmodified oligodeoxynucleotides is limited because they are rapidly degraded. Several structural modifications have therefore been employed to retard oligonucleotide degradation and thereby increase antisense activity. One most often employed has been the replacement of one oxygen of each internucleotide linkage by sulfur, which yields a phosphorothioate oligonucleotide. Phosphorothioate oligonucleotides have frequently been shown exert antisense activity in cultured cells but less often been shown to exert antisense effects in vivo. Antisense activity may be more difficult to achieve in vivo in part because of limited oligonucleotide uptake by target tissues in living animals.

In particular, effective use of antisense oligonucleotides in vivo has been limited in part because it is difficult to achieve adequate cellular uptake of oligonucleotides in target tissues. To date, the most extensive studies of antisense therapy in vivo have been performed in the rat carotid restenosis model. In this model, genes promoting vascular growth have been suppressed by local application of antisense oligonucleotides incorporated into gels or liposomes containing viral proteins in order to increase tissue uptake. Following parenteral administration without special preparation to facilitate tissue uptake, phosphorothioate oligonucleotides have been shown to block increased expression of genes associated with malignant cell proliferation and to retard tumor growth in mice. A single study has demonstrated suppression of a nominal, constituitively expressed host gene following parenteral antisense treatment. This study demonstrated transient (less than 48 hour) reduction in hepatic expression of PKC-alpha in mice receiving intraperitoneal injections of a 20-mer phosphorothioate oligonucleotide.

SUMMARY OF THE INVENTION

We have discovered that phosphorothioate oligonucleotides are taken up by the kidney in large quantity following systemic infusion and remain intact in kidney cells over several days. Autoradiographic studies have shown further that phosphorothioate oligonucleotides taken up by the kidney are localized predominantly in the proximal tubule.

It is an object of this invention, therefore, to provide an oligonucleotide that persists in the treatment of mammalian kidney diseases.

It is another object of this invention to provide a method of treating mammalian kidney diseases and ailments with antisense oligonucleotides.

In one embodiment, this invention is a method for treating diseases involving the mammalian kidney proximal tubule epithelium comprising administering a therapeutic amount of antisense oligonucleotides to a mammal.

In another embodiment, this invention is a method for treating diseases involving the mammalian kidney proximal tubule epithelium consisting of intravenously administering at least one dose of a therapeutic amount of naked antisense composition consisting of at least one phosphorothioate oligonucleotides.

In yet another embodiment, this invention is an antisense composition against mRNA comprising at least one mammalian kidney epithelial protein comprising at least one 18–30-mer phosphorothioate oligonucleotides.

DESCRIPTION OF THE DRAWINGS

FIG. 1 shows that a 2.5 $\mu$M dose of AS1 reduced the NaPi-2/cyclophilin mRNA ration by 41+/−17% (mean of three separate experiments in which 3, 6, and 5 rats received AS1 and a equal number of rats received saline). Similar doses of reversed AS1 (rAS1) and scrambled AS1 (sAS1) had no effect (separate experiments in which 5 rats received oligonucleotides and 5 rats received saline). A 7.5 $\mu$M dose of AS1 also reduced the NaPi-2/cyclophilin mRNA ratio while rAS1 in this dose again had no effect (separate experiments in which 5 rats received oligonucleotides and 5 rats received saline). As compared to rats maintained on a low phosphorous diet, the NaPi-2/cyclophilin mRNA ratio was also reduced in rats maintained on normal chow (NC) which received no oligonucleotide (n=4 NC rats versus 6 control rats on low phosphorous diet; *, p less than 0.05 versus simultaneous control (assigned 100%)).

FIGS. 8A, 8B, 8C and 8D are autoradiographs (250× magnification) showing internal localization of labeled oligonucleotide at 3 hours (panels A and B, cortex and medulla) and 4 days (panels C and D, cortex and medulla) after intravenous infusion. Uptake at both intervals was confined to proximal tubules with staining not observed in glomeruli, distal tubules, or medullary structures.

DESCRIPTION OF THE CURRENT EMBODIMENT

Figure 1:
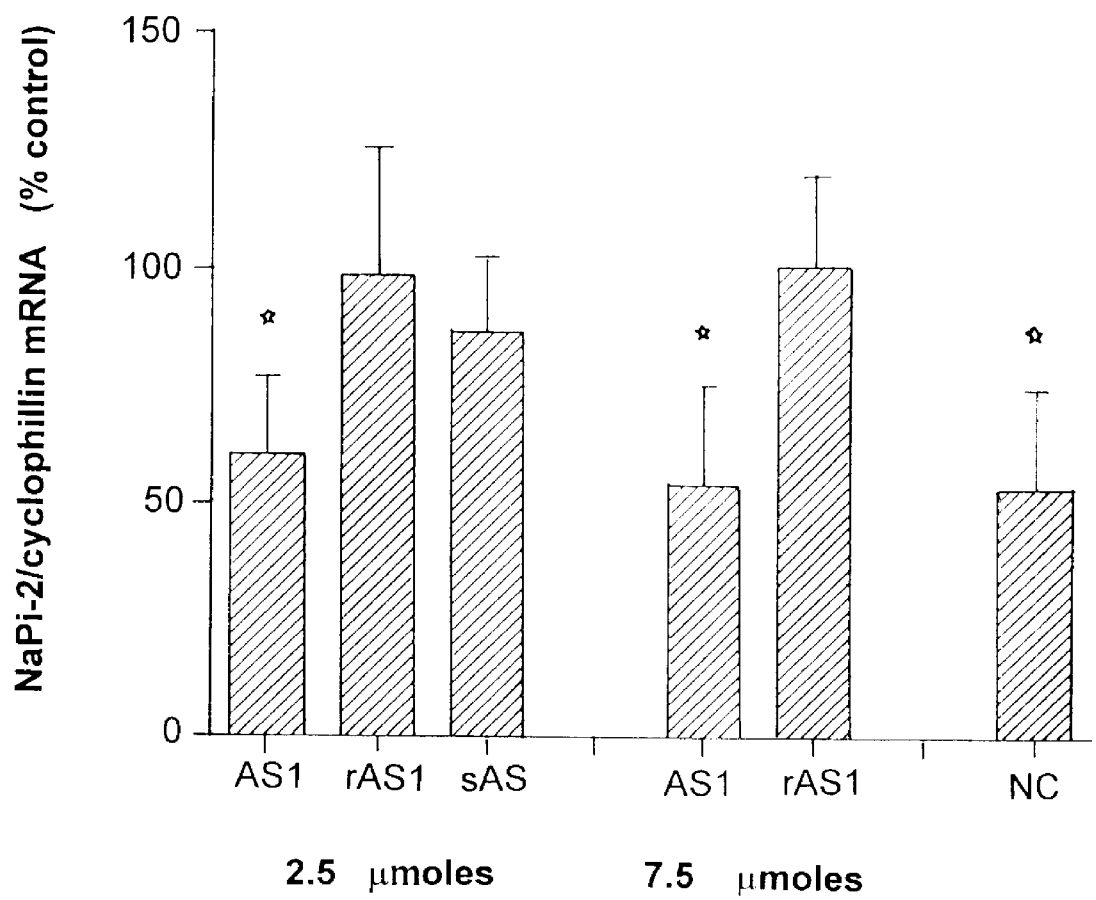
FIG. 1 is a plot of NaPi-2 to cyclophilin message ratios in the kidneys of rats after oligonucleotide treatment expressed as a percent of the control ratio observed in rats receiving in saline.

The present invention relates to an antisense oligonucleotide that persists in a non-degraded form in mammalian kidneys and to a method for using the antisense oligonucleotide to treat renal disorders.

The antisense oligonucleotide of this invention has been found to persist in a non-degraded state in tubular epithelium for a sustained period of time making the antisense oligonucleotide useful for therapies involving subacute and chronic renal conditions. The use of specific antisense oligonucleotides of this invention inhibit mRNA and, thus, protein synthesis of transporter protein in the kidney including the sodium/phosphate cotransporter.

The use of antisense against the $Na/PO_4$ cotransporter blocks phosphate uptake by the proximal tubule. This discovery is useful for treating diseases associated with elevated serum phosphate, hyperphosphatemia. Hyperphosphatemia is observed in a variety of renal diseases including inflammatory, metabolic, and genetic—in which glomerular filtration and/or renal blood flow are diminished. As portions of the kidney are damaged, phosphate is not efficiently excreted. The retention of phosphate in the blood is excaberated by the transport activity of remaining intact nephrons. Inhibiting the cotransporter with antisense therapy enhances excretion of phosphate which, in turn, combats hyperphosphatemia.

The antisense oligonucleotides of this invention can also be directed against the mRNA of epithelial or renal interstitial proteins whose function directly contributes to the cause of or expression of a variety of systemic or renal diseases. Targets for the antisense oligonucleotides and methods of this invention include renin or angiotensin II receptors that are responsible for several forms of hypertension. Antisense against transcription factors including cyclins and cycle dependent kinases are useful for treating renal cell carcinoma or other diseases associated with proliferation of epithelial or interstitial cells.

Polycystic kidney disease is yet another target of the antisense oligonucleotides and methods of this invention. Polycystic kidney disease is characterized by the progressive expansion of cysts that eventually destroy the kidney. The cysts are derived from proximal tubule epithelium. Cyst expansion is driven by epithelial proliferation and chloride secretion mediated by the CFTR, cystic fibrosis transregulatory element, protein. Antisense against the mRNA of either transcription factor proteins of the CFTR or both would be taken up by the cystic epithelium where it would block cyst expansion.

Other epithelial targets for antisense include major histocompatibility antigens, for use in allografts or xenografts; transforming growth factor beta and its receptor to prevent nephrosclerosis; tumor necrosis factor or its receptors to prevent nephrosclerosis; and interleukin-6 and its receptor to prevent nephrosclerosis.

The antisense composition of this invention may be administered continuously, intermittently, or just once. In a preferred method, the antisense oligonucleotide will be administered every three to seven days to take advantage of the unexpectedly long half-life of the antisense in the proximal tubule.

The composition may be administered in any manner that targets the kidney proximal tubule epithelium. Preferred methods of administering the antisense composition include intravenously and by retrograde perfusion of the kidney via the ureter and other components of the urine collecting system.

The antisense agent used in the method of this invention is referred to as "naked" antisense. That is, the antisense composition is capable of targeting the appropriate protein without the use of liposomes. Furthermore, the antisense composition delivered by the method of this invention is remains effective for many days.

The method and composition of this invention may be used in conjunction with therapies directed at treating diseases involving mammalian kidneys, including the human kidney. By involving, it is meant that the diseases originate from or involve the mammalian kidney proximal tubule epithelium and the adjacent interstitium. Diseases involving the kidney glomerus and distal tubules are not amenable to this therapy and are not included in the definition of the term "invloving."

EXAMPLE I

The example was designed to elucidate the renal kinetics of a systemically infused 18-mer phosphorothioate oligonucleotide. In particular, this example localized oligonucleotide uptake within the kidney and determined the stability of oligonucleotide in mammalian kidney cells following a single systemic infusion.

Oligonucleotide. Studies were carried out with an 18-mer phosphorothioate nucleotide of molecular weight 5722 Da and SEQ ID NO: 1 5'-ATC-TTC-CAT-AGT-TAG-TCA-3'. This sequence is antisense against human cdc2 starting at base 118 of the cDNA sequence published by Lee and Nurse, *Nature*, 327 31–35 (1987). To facilitate kinetic studies, the oligonucleotide was initially radiolabeled with $^{35}S$ during synthesis to an activity of 1250 $\mu Ci/\mu$mole.

Clearance studies. The plasma clearance of labeled oligonucleotide was assessed in two groups of male Sprague Dawley rats weighing 370–460 grams. Rats were anesthetizes with Inactin (100 mg/kg body weight i.p.) and placed on a temperature regulated table. A PE-50 catheter was inserted into the left femoral artery and used for subsequent blood sampling and estimation of mean pressure. After tracheotomy, PE-50 catheters were inserted into the right and left jugular veins for infusion of rat plasma, normal saline, oligonucleotide, and inulin. Plasma was infused in an amount equal to 1% body weight over 45 min, followed by a reduction of the infusion rate to 0.4 ml/h for the duration of the study. Normal saline was infused at 1.2 ml/h throughout the study. The left ureter was exposed through a midline abdominal incision and a PE 10 catheter was installed for urine collection.

In both groups of rats a constant infusion of oligonucleotide was begun after 90 minutes and continued for 150 minutes. The first group of rats (n=5) received labeled oligonucleotide at the rate of 119 ng/min. The second group of rats (n=4) received the same amount of labeled oligonucleotide along with addition of unlabeled oligonucleotide to achieve a total oligonucleotide infusion rate of 17.5 µg/min. Blood samples were obtained every thirty minutes over five hours, beginning at the initiation of oligonucleotide infusion and continuing for 150 minutes after the cessation of oligonucleotide infusion. Beginning at approximately 120 minutes, 10% inulin (Iso-tex Diagnostics, Friendswood Tex.) was infused with the normal saline and 30 minutes urine samples were obtained between blood samples for measurement of inulin clearance.

Distribution of intravenously infused oligonucleotide. At the close of clearance studies, kidneys and samples of liver, plasma, lung, and spleen were obtained. Tissue content of $^{35}S$ was determined by scintillation counting tissue samples homogenized in water (100 mg tissue per ml). Quenching experiments showed that the counting efficiency in 20 µliter samples of tissue homogenates was greater than 90%. Urinary excretion of $^{35}S$ was also assessed by scintillation counting.

Studies were carried out over 4 days in a group of rats to assess the tissue distribution of oligonucleotide at a later interval after intravenous infusion. Male Sprague Dawley rats weighing 300 to 390 grams were anesthetized briefly with Brevital, 50 mg/kg, i.p. and a catheter was installed in the left jugular vein. After infusion of 86 µg of labeled oligonucleotide over 80 minutes the catheter was removed and the rats were placed in metabolic cages. Urine was collected for 4 days and the rats were then sacrificed and tissue distribution of $^{35}S$ was determined as described above.

The extent of oligonucleotide degradation in tissue and urine samples was by PAGE. Weighed tissue samples were homogenized in buffer (0.5% SDS/10 mM NaCl/20 mM TRIS, pH 7.6, 10 mM EDTA) and treated with Proteinase K (2 mg/ml) for two hours at 37° C. Proteinase digests were extracted twice with phenol/chloroform and once with chloroform. The final extracts were concentrated on microfilter discs with a cut-off of 3,000 Da (Microcon 3, Amicon, Beverly, Mass.) before application to 20% polyacrylamide gels containing 7M urea. Following electrophoresis, the gels were fixed in 10% acetic acid/10% methanol, dried, and subjected to autoradiography.

Micropuncture studies. Glomerular filtration and tubular handling of intravenously infused oligonucleotide was further assessed by micropuncture in Munich Wistar rats (n=4). Male rats weighing 300 to 350 grams were prepared for renal function studies as described above, except that the oligonucleotide infusion was begun after 70 minutes and continued at a rate of 2.4 µg/min for 210 minutes. Timed (4–7 minute) tubule fluid samples were obtained during two to three clearance periods beginning 40 minutes after initiation of oligonucleotide infusion. Samples were obtained from Bowman's space (3–5 samples per rat) and the distal tubule (2–5 samples per rat). Distal tubule segments were identified by preliminary injection of 1% lissamine green through pipettes of 4 micron outer diameter. The volume of tubule fluid samples was determine by injecting the samples into light mineral oil. The diameter of the droplet formed by each sample was assessed by light microscopy and the volume of the droplet then calculated by its assuming its shape was spherical. Following volume determination, the tubule fluid droplets were transferred to scintillation vials and their $^{35}S$ content was assessed. The accuracy of volume determinations was confirmed by the findings of 97+/−3% of predicted counts in measured droplets of a standard solution of labeled oligonucleotide. The total load of labeled filtered over the course of the 210 minute oligonucleotide infusion in each rat was obtained as the area under the curve:

[label]$_{plasma}$·GFR·TF/P Bowman's space where values for the concentration of label in the plasma, [label]$_{plasma}$, were obtained by curve fitting from plasma levels measured at 30–50 minute intervals.

Autoradiogrphic studies. Localization of oligonucleotides within the kidney was assessed by autoradiography. Kidneys were harvested at three hours after oligonucleotide infusion in two rats and at four days after oligonucleotide infusion in three rats. Labeled oligonucleotide was as described above except that the dose infused into rats studied at 4 days was increased to 326 µg. Kidneys were fixed by retrograde aortic perfusion with 1.25% glutaraldehyde in 0.1M cacodylate buffer (pH 7.4). For light microscopic autoradiography, coronal slices of kidney tissue were embedded in paraffin and 5 micrometer sections were mounted on slides and coated with emulsion (NTB2, Kodak, Rochester N.Y.). After three weeks of exposure, the slides were developed, dried, and stained with hematoxylin and eosin. A semiquantitative scoring system was used to compare uptake of labeled oligonucleotide in very early and later proximal nephron segments in two sections from each rat. Individual tubule profiles were scored 0 (no grains above background) to 3+ (dense grains). The average score in sections of very early segments of the proximal nephron, identified by visible transformation of the tubule into the parietal epithelium of a glomerulus, were compared with the average scores in sections of the proximal nephron selected at random by positioning the microscope stage without looking at the specimen. For electron autoradiography, small blocks of cortical tissue were embedded in Epon and 60–100 nm sections were mounted on grids and coated with emulsion (IL4, Ilford, Essex, UK). After three weeks of exposure, sections were developed fixed and counterstained with lead citrate and uranyl acetate.

Results. The tissue distribution of $^{35}S$ following intravenous infusion of labelled oligonucleotide is summarized in Table 1 below.

| | Distribution of Intravenously Infused Oligonucleotide | | | | | |
|---|---|---|---|---|---|---|
| | 5 hrs | | | | 4 days | |
| | 18 µg infused n = 5 | | 2414 µg infused n = 4 | | 86 µg infused n = 4 | |
| | % dose | % dose per gram | % dose | % dose per gram | % dose | % dose per gram |
| Kidney | 21.2 ± 2.7 | 7.4 ± 0.8 | 11.2 ± 0.9 | 3.8 ± 0.3 | 2.9 ± 0.5 | 1.3 ± 0.2 |
| Liver | 17.4 ± 1.6 | 1.3 ± 0.3 | 12.4 ± 1.9 | 0.9 ± 0.2 | 3.9 ± 0.5 | 0.3 ± 0.1 |
| Plasma | 3.2 ± 0.5 | 0.3 ± 0.1 | 5.2 ± 0.6 | 0.4 ± 0.1 | <0.1 | <0.1 |
| Urine | 17.6 ± 0.9 | | 17.0 ± 1.9 | | 63.5 ± 2.7 | |

Figure 5:
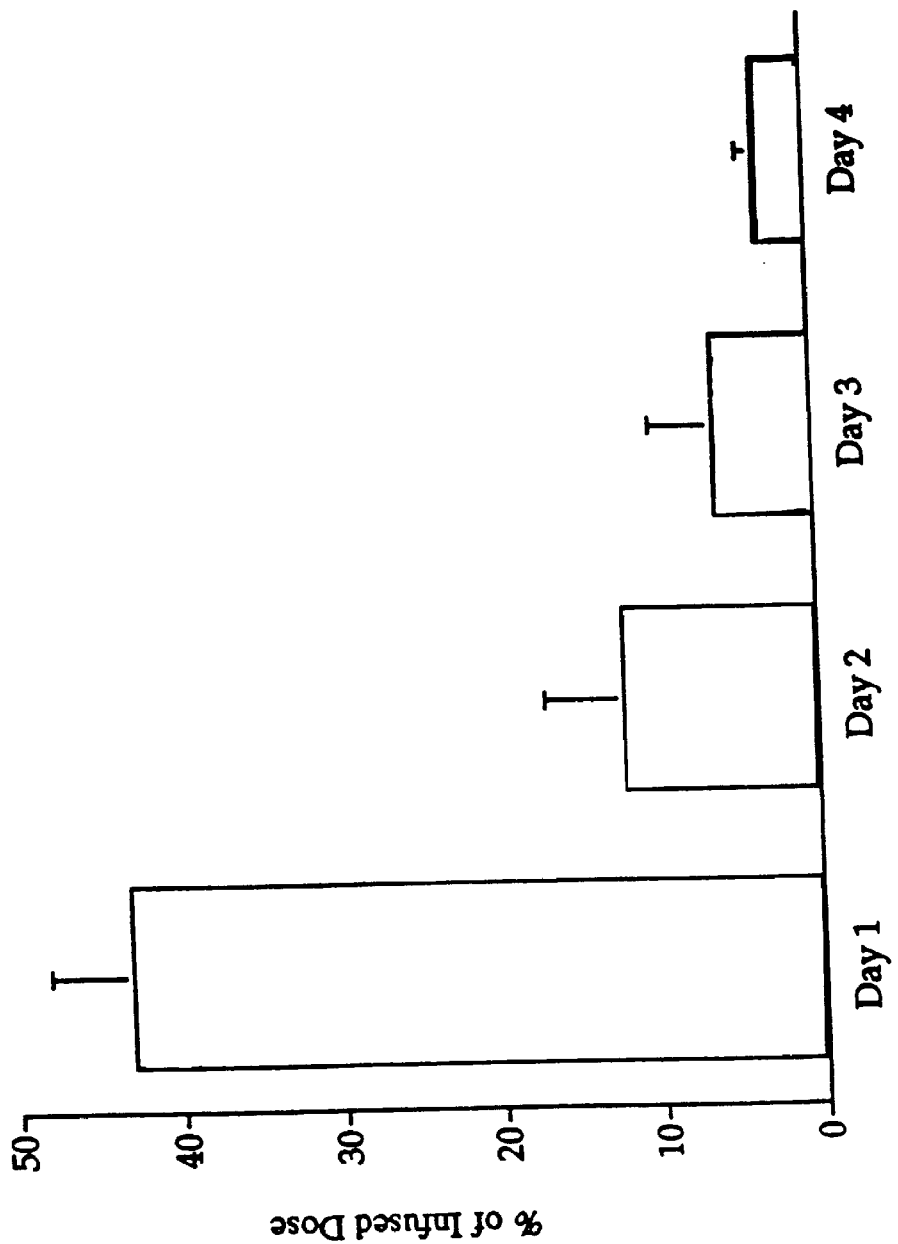
FIG. 5 is a plot of urine excretion of $^{35}$S oligonucleotide label over four days following intravenous infusion in rats.

In rats sacrificed 5 hours after infusion of 16 μg oligonucleotide, the largest portion of the infused label was found in the kidney. A slightly lesser amount was found in the liver. Only a small amount of the infused label remained in the plasma while an amount similar to that found in the kidneys and liver was excreted in the urine. Expression of tissue content of infused label per gram organ weight revealed that the concentration of label in the kidney was more than twenty fold greater that the concentration of label in the plasma and more than five fold greater than the concentration of label in the liver. The concentration of label in lung and spleen was less than that in the plasma (data not shown). Prominent uptake of label in the kidney was again observed in rats sacrificed 5 hours after infusion of 2414 μg of oligonucleotide. The fraction of infused label found in the kidney and liver in these animals was less than in animals which received a much smaller amount of oligonucleotide, but the concentration of label in the kidney again greatly exceeded that in the liver and plasma. The fraction of label excreted in the urine over five hours was similar when rats received 2414 μg of oligonucleotide as when they received 18 μg of oligonucleotide. Studies performed at four days after oligonucleotide infusion showed that significant portions of label remained in the kidney and liver while no label was detectable in the plasma. The concentration of label in the kidney again exceeded that in the liver. Over four days, the majority of the infused label was excreted in the urine. Urine excretion of label was greatest over the first day and declined progressively, as illustrated in FIG. 5.

Figure 6:
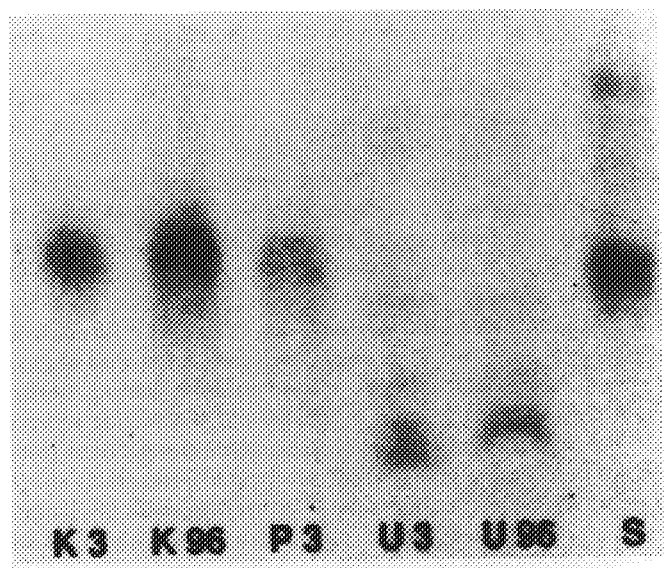
FIG. 6 is a PAGE analysis of kidney tissue, plasma, and urine after intravenous oligonucleotide infusion. Intact oligonucleotide with size equal to that in the infusate (S) was found in the kidney at 3 hours and 96 hours (K3 and K96) and in the plasma at 3 hours (P3). In contrast, intact oligonucleotide was not detected in the urine at either interval (U3 and U96). Plasma concentration of label was too low for PAGE analysis at 96 hours.

Results of PAGE analysis of kidney tissue, plasma, and urine obtained 3 hours after oligonucleotide infusion and of kidney tissue and urine obtained 4 days after oligonucleotide infusion are illustrated in FIG. 6. The appearance of label in a single band with size equivalent to the infused 18-mer indicated that oligonucleotide taken up by the kidney remained largely intact at both 3 hours and 4 days and that oligonucleotide in the plasma remained largely intact at 3 hours. In contrast, intact oligonucleotide was not found in the urine at either interval. Similar results were obtained in four rats sacrificed at 3 hours and two rats sacrificed at 4 days.

Figure 7:
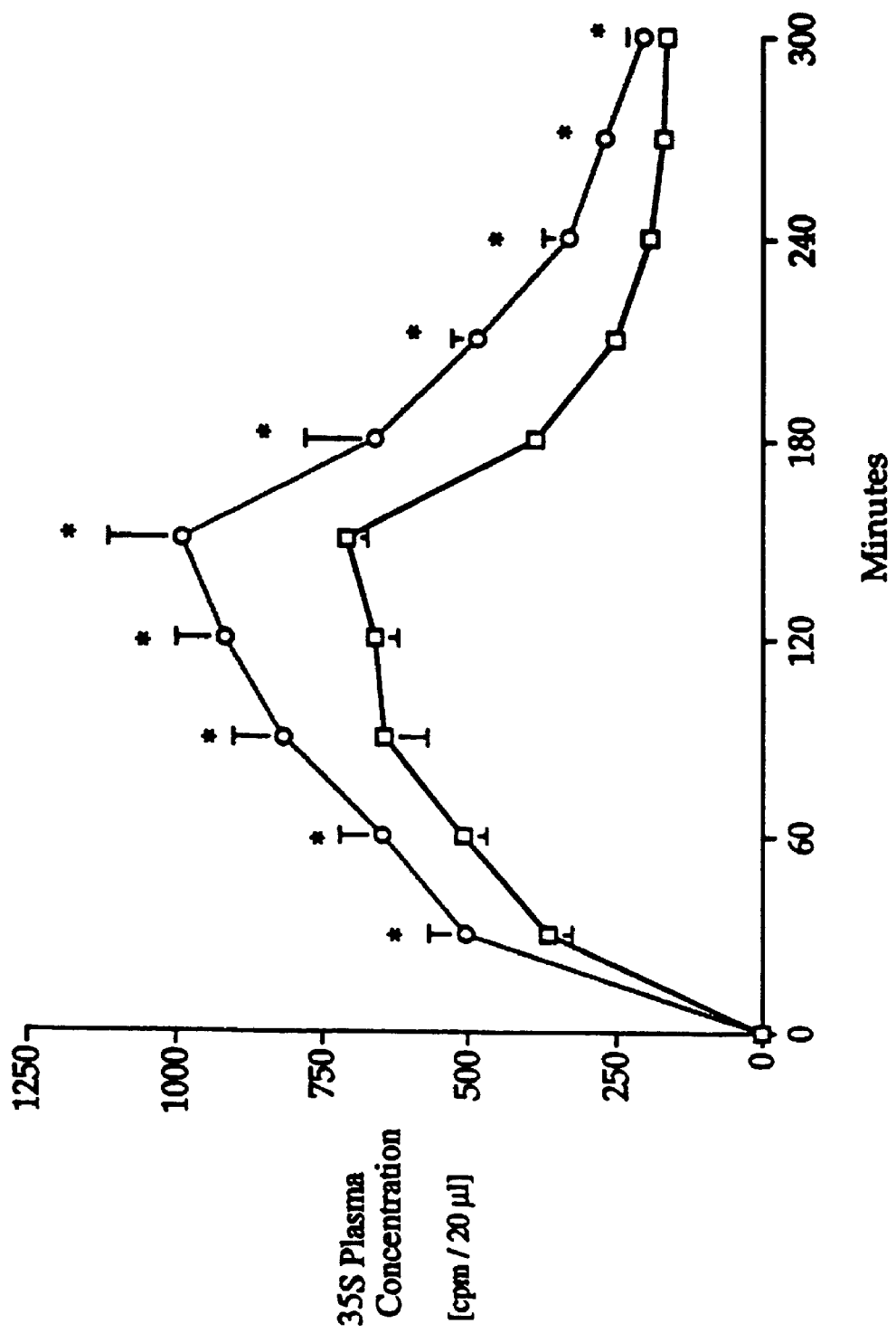
FIG. 7 is a plot of plasma concentration of $^{35}$S oligonucleotide label in rats receiving a constant infusion of oligonucleotide over 150 minutes, illustrating rapid plasma clearance following discontinuation of the infusion. Plasma levels of labeled oligonucleotide was infused with cold oligonucleotide (o, total infusion rate 17.5 $\mu$g/min) than when the same amount of labeled oligonucleotide was infused alone (☐ infusion rate 119 ng/min; *, p less than 0.05).

Plasma levels of labeled oligonucleotide observed during and after constant infusion of oligonucleotide for 150 minutes are depicted in FIG. 7. Oligonucleotide concentration increased rapidly over the first 30 minutes of infusion and appeared to be approaching a plateau at 150 minutes. The addition of a large excess of cold oligonucleotide resulted in plasma levels of labeled oligonucleotide that were only slightly greater than those observed during infusion of oligonucleotide alone. The peak plasma oligonucleotide concentration achieved during infusion of labeled oligonucleotide alone, calculated from the specific activity, was 37+/-2 nM Presuming no difference in the clearance of cold and labeled oligonucleotide, the peak plasma oligonucleotide concentration achieved during their combined infusion was 6.9+/-0.2 μM. Infusion of an 147-fold greater quantity of oligonucleotide thus resulted in an 186-fold increase in the plasma oligonucleotide concentration, indicating that plasma clearance was reduced only slightly as oligonucleotide concentration increased. Consistent with this conclusion, plasma oligonucleotide clearance rates over the final 30 minutes after discontinuation of the infusion were 0.32+/-0.01 ml/min/400 g in the rats receiving only labeled oligonucleotide and 0.26+/-0.04 ml/min/400 g in rats receiving an excess of cold oligonucleotide along with labeled oligonucleotide (p<0.05). These mean values for plasma 5 oligonucleotide clearance rate were much less than the corresponding mean values for GFR (1.95+/-0.18 ml/min/400 g and 2.13+/-0.14 ml/min/400 g) but greater than mean values for clearance of plasma oligonucleotide label into the urine (0.07+/-0.02 ml/min/400 9 and 0.04+/-0.01 ml/min/400 g). Examination of a logarithmic plot of oligonucleotide concentration suggested that oligonucleotide clearance was reduced by 120 minutes following discontinuation of the low dose infusion, but the experiments were not carried out long enough to calculate accurate plasma clearance rates at this interval.

Micropuncture studies were performed to determine whether intravenously infused oligonucleotide was filtered by the glomerulus and then reabsorbed. Values for physiologic parameters including GFR (1.50+/-0.12 ml/min), mean arterial pressure (110+/-5 mmHg), and hematocrit (44+/-2) in rats subjected to micropuncture were similar to values previously obtained in normal animals. Results of micropuncture measurements are summarized in Table 2, below.

| Micropuncture Study Summary | | |
|---|---|---|
| Tubule Fluid Flow Rate nl/min | $[\text{label}]_{tubule\ fluid}$ / $[\text{label}]_{plasma}$ | Fractional Delivery % |
| Bowman's Space 50 ± 2 | 0.07 ± 0.03 | (100) |
| Distal Tubule 18 ± 2 | 0.06 ± 0.02 | 34 ± 19* |
| Urine | 3.20 ± 0.42 | 21 ± 8* |

Mean ± SD; *, p < 0.05 vs Bowmans's space.

SNGFR, measured as the rate of fluid collection from Bowman's space, averaged 50+/-2 nl/min and the tubule fluid to plasma concentration ratio of label in Bowman's space averaged 0.07+/-0.03. Distal tubule fluid delivery averaged 18+/-2 nl/min and the tubule fluid to plasma concentration ratio of label averaged 0.06+/-0.02, while the urine to plasma concentration ratio of label averaged 3.20+/-0.42. Taking the delivery of label to Bowman's space as 100%, values for the fractional delivery of label averaged 34+/-19% in the distal nephron and 21+/-8% in the urine. Delivery of filtered label into the urine was not significantly less than delivery of filtered label to the distal tubule, so that reabsorption of label beyond the distal micropuncture site was not detected. The portion of the intravenously infused label entering Bowman's space during the 210 minute infusion period was estimated to be 58+/-26%. This value exceeded the combined portion of the infused label returned in the kidneys and excreted in the urine, which averaged 23+/-4% in rats subjected to micropuncture.

Figure 9:
FIG. 9 is an electron microscope autoradiograph (5250× magnification) showing the uptake of labeled oligonucleotide in the proximal tubule after 3 hours of intravenous infusion.

Results of autoradiographic studies are illustrated in FIGS. 8 and 9. At 3 hours after oligonucleotide infusion, light microscopic autoradiography revealed prominent uptake of oligonucleotide in proximal tubules (FIG. 8A). Deposition of oligonucleotide was not detected in glomeruli, distal tubules, or in the medulla (FIG. 8B). Of note, the pattern of oligonucleotide uptake in proximal tubules was uneven. Semiquantitative scoring revealed that uptake of oligonucleotide was more prominent in the earliest portion of the tubule as identified by visible transformation of the tubular epithelium into Bowman's capsule, than in randomly selected proximal tubule profiles (mean score: 2.2+/-0.8 vs 1.3+/-0.9, p<0.01). The pattern of oligonucleotide uptake, as assessed by light microscopic autoradiography, remained the same at 4 days after oligonucleotide infusion (FIGS. 8C and 8D). Significant uptake was again observed only in the proximal tubules, and uptake was greater in the earliest portion of the tubule than in randomly selected tubule profiles (mean score: 2.2+/−0.9 vs 1.3+/−1.0, p<0.01). Electron microscopic studies revealed that within 3 hours after infusion, oligonucleotide was taken up into proximal tubule cells and not simply bound to brush border (FIG. 9.) Oligonucleotide distribution did not appear to be confined exclusively to any compartment within proximal tubule cells, and was not notably different in electron micrographs prepared from tissue obtained at 3 hours and 4 days after infusion.

This example demonstrated that there is a high concentration of a phosphorothioate oligonucleotide within the kidney at three hours following intravenous infusion as summarized in Table 1. A lesser but still significant fraction of the infused dose of oligonucleotide remained present within the kidney at 4 days following oligonucleotide administration. Gel electrophoresis showed, moreover, that the majority of the oligonucleotide present in the kidney at both 3 hours and 4 days after administration was in the form of the intact 18-mer. These findings show that intravenously infused oligonucleotides could exert antisense activity in the kidney, presuming they are taken up into an appropriate cellular compartment.

While intact oligonucleotide was found in the kidney, no intact oligonucleotide was found in the urine in this example. This example does not reveal whether excretion of label in the urine was the result of oligonucleotide degradation in the kidney, or whether oligonucleotide was degraded in other tissues and labeled degradation products then excreted by the kidney. An index of the contribution of the kidney to total plasma oligonucleotide clearance, however, was obtained by adding the portion of label found in the kidney to the portion of label found in the urine. In rats studied over 5 hours, the kidney and urine together contained 39+/−3% of the infused dose when 18 micrograms was administered and 28+/−3% of the infused dose when 2414 micrograms was administered. These findings indicate that, while the portion of the infused label found in kidney tissue and urine was large, the kidneys were not solely responsible for the clearance of intravenously infused oligonucleotide.

Kinetic studies carried out over 5 hours also showed that the plasma oligonucleotide clearance rate was considerably less than the GFR. This finding established that the oligonucleotide infused, which had a molecular weight of 5722 Da, either was not freely filtered at the glomerulus or was extensively reabsorbed in the nephron. Micropuncture studies revealed that the concentration of oligonucleotide label in Bowman's space averaged only 7+/−3% of that in plasma, indicating that glomerular filtration of oligonucleotide was restricted The binding of oligonucleotides to plasma proteins probably accounts for the restricted filtration oligonucleotides in glomerulus. In this example, the estimated delivery of oligonucleotide into the nephron, though limited by plasma protein binding, exceeded the amount of oligonucleotide label retained in the kidney and excreted in the urine. This finding indicates that filtered oligonucleotide label was reabsorbed into the circulation as well as retained by kidney cells. Micropuncture studies indicated that reabsorption of label was largely accomplished prior to the accessible distal nephron. It should be noted that reabsorption of label could have represented reabsorption of oligonucleotide degradation products as well as reabsorption of intact oligonucleotide. Rates of filtration and reabsorption of label measured in this example provide only upper bounds for the rates of filtration and reabsorption of intact phosphorothioate oligonucleotide.

Light microscopic autoradiography showed that the intact oligonucleotide retained in the kidney was localized in the proximal tubule. These results showed, moreover, that retention of oligonucleotide was most prominent in the early portion of the tubule. Electron microscopy showed that oligonucleotide retained by the kidney was taken up by proximal tubule cells and not merely adherent to the brush border or other portions of the cell membrane. These results indicate that intact oligonucleotides filtered by the glomerulus are taken up from the tubule lumen into proximal tubule cells. Molecules in the size range of oligonucleotides, including peptide hormones and small proteins, are known to be handled by the kidney in this manner. Such peptide molecules have been shown to be taken up into the proximal tubule by receptor mediated endocytosis and then degraded in lysosomes.

Electron microscopic autoradiograms made in the current study also revealed that oligonucleotides taken up in the proximal tubule were not localized exclusively within endocytic vesicles and lysosomes. These results indicate that a high concentration of oligonucleotide was achieved in the proximal tubule and that a major portion of the oligonucleotide taken up by the proximal tubule remained intact over four days.

This is the first demonstration that antisense oligonucleotides, intraveneously administered, localize to the proximal tubules of the nephron.

EXAMPLE II

This example was designed to determine whether phosphorothioate oligonucleotides cleared from the circulation by the kidney could exert antisense effects in proximal tubule cells.

Oligonucleotides. Experiments were conducted with 18- and 20-mer phosphorothioate oligonucleotides. Three oligonucleotides, denoted AS1, AS2, and AS3, were designed to hybridize with MRNA for NaPi-2. AS1 had the SEQ ID NO: 1 of 5'° CTC-GCT-GTA-GGA-CAT-CAT 3' corresponding to positions 64–81 of the NaPi-2 cDNA, AS2 had the sequence SEQ ID NO: 2 of 5' TCC-CCC-CAA-TCT-CTC-GCT-GT 3' corresponding to positions 54–73 of the cDNA, and AS3 had the SEQ ID NO: 3 of 5' GCA-CCC-ACA-ATG-AGT-CCT 3'POS 3' corresponding to positions 31–48 of the CDNA. Target sequences were in each case close to the presumed translation initiation site (positions 54–59). A scrambled sequence of AS1, SEQ ID NO: 4 of , 5' CTC-ACA-CCT-TGC-GCT-CTC-CT 3', and the reversed sequence of AS1 SEQ ID NO: 5, 5' TGT-CGC-TCT-CTA-ACC-CCC-CT 3', were used as controls. Oligonucleotides were prepared using amidite chemistry and obtained commercially (Oligos Etc., Wilsonville, Oreg.).

Treatment of rats with oligonucleotides. Oligonucleotides were given to male Sprague Dawley rats weighing 270–330 g. Rats were placed on a low phosphate diet (0.07% phosphorous, Teklad, Madison, Wis.) for three days prior to oligonucleotide administration. They were then anesthetized with Brevital, 50 mg/kg intraperitoneally, and maintained on a temperature regulated table while a single dose of oligonucleotide dissolved in 3 mi of 0.9% NaCl was infused into the left jugular vein over 2 hours. Control rats received saline alone. Following oligonucleotide or saline administration, rats were continued on the low phosphate diet for a further three days. They were then anesthetized with Inactin, 100 mg/kg intraperitoneally, and kidney tissue was obtained for Northern blotting, Western blotting, and brush border membrane vesicle transport studies. Additional Northern analyses were carried out in a group of rats which were maintained on nominal laboratory chow (1.0% phosphorous) and received a control saline infusion.

Northern analysis: Total RNA (~15 µg) from whole kidneys was denatured, electrophoresed on 1% agarose/formaldehyde gels and transferred to nylon membranes by vacuum blotting. The membranes were exposed to UV-light for 2 minutes to crosslink the RNA. Full length cDNA probes for NaPi-2, (Maganin, S. et al; *Proc. Natl. Acad. Sci. USA* 90, 5979–83 (1993) and cyclophilin, were random primer labeled using [alpha-32P]dCTP (Gibco-BRL kit, Gaithersburg, Md.). Blots were prehybridized and then hybridized for 12 hours at 65° C. in buffer containing 0.5M $NaHPO_4$ pH=7.2, 7% SDS, and 1 mM EDTA. Blots were then washed once at room temperature and twice at hybridization temperature in high stringency buffer (5% SDS, 1×SSC) and analyzed by exposure to x-ray films and densitometry (Ultrascan Laser, LKB Bromma) or by phosphor imaging (Molecular Dynamics 445 SI, Sunnyvale, Calif.).

Western analysis. Brush border membrane vesicles were prepared from kidney cortex using the $MgCl_2$ precipitation method (Brown, C. D. A. et al.; *Biochem. Biophys. Acia* 769, 471–78 (1984). Samples of these vesicles were subjected to Western analysis. SDS polyacrylamide get electrophoresis was performed as described by Laemmli, *Nature* (Lond.) 227, 680–685 (1970), using 9% acrylamide gels. Before electrophoresis, samples were diluted in buffer (8% SDS, 4 mM EDTA, 40% glycerol, 0.38M Tris/HCl, pH 6.8, 0.1% bromophenol blue) and proteins were denatured by boiling for two minutes. Electrophoretic transfer to nitrocellulose membranes (Schleicher & Schuell, Keene NH) was performed as described by Towbin et al, *Proc. Natl. Acad. Sci. USA*, 76, 4350–54 (1979). Membranes were then blocked for two hours at room temperature (5% milk powder, 1% Triton-X in TBS-buffer; TBS-buffer: 25 mM Tris/HCl pH=7.4, 150 mM NaCl) and incubated overnight with polyclonal antisera directed against a synthetic COOH— terminal peptide of NaPi-2 at a dilution of 1:4000. Binding of the primary antibody was detected using a peroxidase conjugated goat anti-rabbit IgG (Sigma Chemicals, St. Louis Mo.) followed by application of a chemiluminescence detection system (ECL, Amersham, Arlington Heights, Il.) and exposure to x-ray film.

Brush border membrane vesicle transport. The transport of $[^{82}P]$ phosphate (0.1 mM) and $[^{35}S]$ sulfate (0.1 mM) into isolated brush border membrane vehicles was measured in triplicate in the presence of 100 mM mannitol, 10 mM Tris-HEPES, pH 7.4, and either 100 mM KCl or 100 mM NaCl and described by Brown et al, supra. The sodium dependent component of transport was calculated as the difference in transport in the presence NaCl and KCl.

Statistics. Values are presented as the mean +/− sd. The unpaired t test was used to assess the significance of differences in experiments containing two groups and the ANOVA and Fischer's exact test were used to assess the significance of differences in experiments containing more than two groups.

Figure 2:
FIG. 2 is a Northern analysis of NaPi-2 message expression in rats receiving 2.5 $\mu$moles of oligonucleotides. In comparison with saline infusion in simultaneously prepared control rats (C) AS1 reduced NaPi-2 message expression while reversed AS1 (rAS1) had no effect.

Results. The effects of systemic infusion of oligonucleotides on renal expression of message for NaPi-2 are depicted in FIGS. 1 and 2. Experiments were performed first with 2.5 µmole doses of oligonucleotides. Densitometric analysis showed that at this dose oligonucleotide AS1 reduced the NaPi-2 mRNA to cyclophilin mRNA ratio by an average of 40+/−17%. This overall result was obtained in three separate experiments in which the NaPi-2 to cyclophilin mRNA ratio was reduced by 46+/−10, 42+/−19, and 29+/−25, respectively. In contrast, the reversed sequence of AS1 (rAS1) and a scrambled sequence of AS1 (sAS1) did not effect renal NaPi-2 mRNA levels. NaPi-2 mRNA levels were likewise not significantly reduced by 2.5 µmoles of the antisense oligonucleotides AS2 and AS3 (not shown). The NaPi-2 mRNA to cyclophilin mRNA ratio was, however, lower in a group of rats maintained on nominal chow (NC) than in control rats maintained on the low phosphorous diet, as has previously been described. Administration of an increased dose of 7.5 µmoles of AS1 reduced the NaPi-2 to cyclophilin mRNA ratio by 46+/−21% while infusion of an equal dose of reversed AS1 had no effect. Systemic infusion of oligonucleotides had no effect on body weight, which was not different in oligonucleotide and saline infused rats in any experiment.

Figure 3:
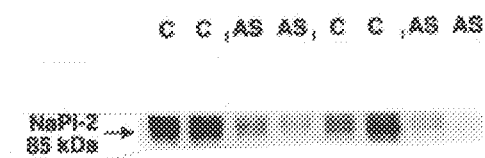
FIG. 3 is a Western analysis of brush border membrane proteins in rats receiving 7.5 $\mu$moles of oligonucleotides. In comparison with saline infusion in simultaneously prepared control rats (C) AS1 reduced the expression of 85 kDa protein detected by a polyclonal antibody raised against a peptide sequence of NaPi-2.

Western analysis of brush border membrane proteins obtained from rats receiving 7.5 µmoles of oligonucleotides is illustrated in FIG. 3. Densitometry showed that staining of the 85 kDa protein recognized by antibody raised against NaPi-2 peptide was reduced by AS1 (40+/−19% of control, p<0.05) but not by reversed AS1 (102+/−24% of control). Densitometry did not, however, reveal a significant reduction in the 85 kDa protein in vesicles from rats which received 2.5 µmoles of AS1 (57+/−30% of control, p>0.05, not illustrated).

Figure 4A:
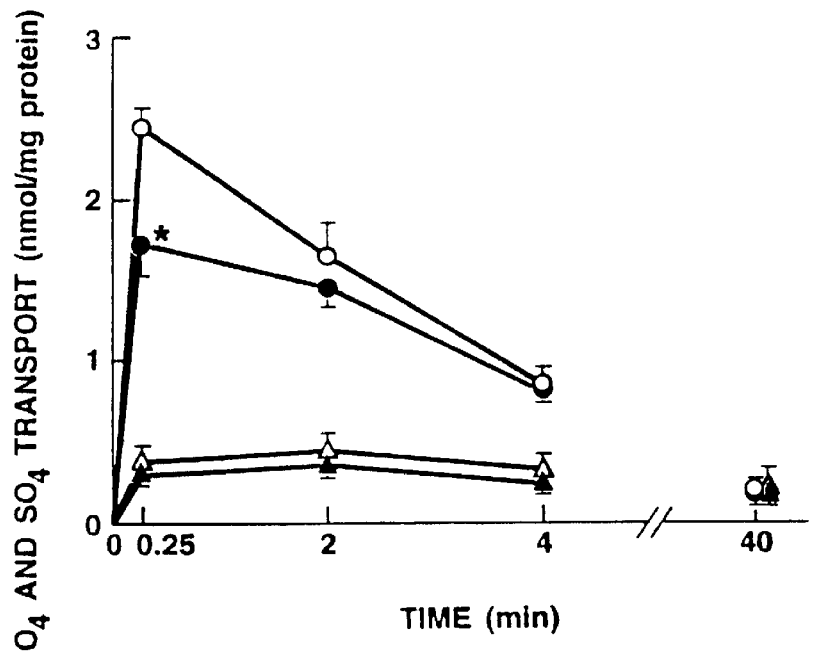
FIG. 4 is a time plot of the uptake of phosphate (○, ●) and sulfate (Δ, ▲) in brush border membrane vesicles. Closed symbols denote values in rats receiving 75 $\mu$moles of oligonucleotides (AS1, top panel, or reversed AS1, bottom panel) while open symbols denote values in simultaneously prepared saline infused controls. AS1 reduced the rate of phosphate but not sulfate uptake in membrane vesicles while reversed AS1 had no effect on either parameter. (p less than 0.05 versus control; n=4 oligonucleotide infused rats and 4 controls in each experiment).
Figure 4B:
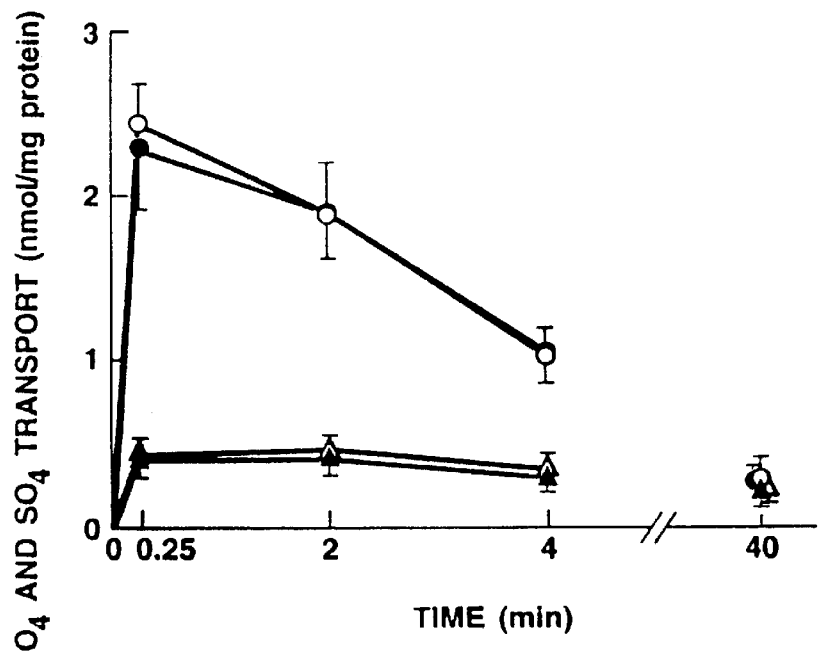

The time course of phosphate and sulfate uptake by brush border membrane vesicles from rats which received 7.5 µmoles of oligonucleotides is depicted in FIG. 4. The initial rate of phosphate uptake was reduced in rats receiving 7.5 µmoles of AS1 but not altered in rats receiving an equal amount of reversed AS1. Vesicle uptake of sulfate, in contrast to phosphate, was not effected by administration of either AS1 or rAS1.

This example has shown that suppression of NaPi-2 message expression by AS1, which was one of three phosphorothioate oligonucleotides designed to hybridize with NaPi-2 mRNA. An advantage of the selection of a transport molecule as the antisense target in this example was that molecular function as well as protein and gene expression could be assessed. This example showed that a dose of 7.5 micromoles of AS1 reduced sodium dependent phosphate uptake and NaPi-2 protein content in proximal tubule brush border membrane vesicles as well as reducing NaPi-2 message expression. The effect of AS1 appeared to be dose dependent, in that a dose of 2.5 micromoles of AS1 did not significantly reduce sodium dependent phosphate uptake or NaPi-2 protein in vesicles, though it did reduce NaPi-2 message expression.

Distinguishing suppression of gene expression mediated by antisense activity from other nonspecific effects of oligonucleotides is a major problem in antisense studies. In the current study, the finding that a reversed sequence of AS1 did not effect vesicle phosphate transport, NaPi-2 protein, or NaPi-2 message expression indicates that the effect of AS1 were attributable to antisense activity. The finding that AS1 reduced phosphate uptake but not sulfate uptake into brush border membrane vesicle provided further evidence that AS1 caused specific suppression of NaPi-2 activity and did not cause generalized suppression of proximal tubule function.

The description above has been offered for illustrative purposes only, and it is not intended to limit the scope of the invention of this application which is defined in the following claims.

What we claim is:

1. A phosphrothioate oligonucleotide consisting of the nucleotide sequence set forth in SEQ. ID. NO: 1.

* * * * *

UNITED STATES PATENT AND TRADEMARK OFFICE
CERTIFICATE OF CORRECTION

PATENT NO. : 5,840,875
DATED : November 24, 1998
INVENTOR(S) : Schreiner et al.

It is certified that error appears in the above-identified patent and that said Letters Patent is hereby corrected as shown below:

At column 7, line 67, delete "5".

At column 10, line 38, delete "5'" " and replace with -- 5' --.

At column 11, line 21 delete "Acia" and replace with -- Acta --.

At column 11, line 44, delete "[$^{82}$P]" and replace with -- [$^{32}$P] --.

Signed and Sealed this

Thirtieth Day of March, 1999

Attest:

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: yes ( x i ) SEQUENCE DESCRIPTION: SEQ ID NO:1:

CTCGCTGTAG GACATCAT      18

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

TCCCCCCAAT CTCTCGCTGT      20

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GCACCCACAA TGAGTCCT      18

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

CTCACACCTT GCGCTCTCCT      20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA (x i) SEQUENCE DESCRIPTION: SEQ ID NO:5:

TGTCGCTCTC TAACCCCCCT                                                                20